United States Patent [19]

Crossley et al.

[11] Patent Number: 4,577,022
[45] Date of Patent: Mar. 18, 1986

[54] SILYL COMPOUNDS

[75] Inventors: Roger Crossley, Reading; Robin G. Shepherd, Maidenhead, both of England

[73] Assignee: John Wyeth & Brother, Ltd., Maidenhead, England

[21] Appl. No.: 506,277

[22] Filed: Jun. 21, 1983

[30] Foreign Application Priority Data

Jun. 25, 1982 [GB] United Kingdom ............... 8218466

[51] Int. Cl.$^4$ ........................................... C07D 215/16
[52] U.S. Cl. ..................................... 546/14; 514/925; 514/926; 514/927; 514/928
[58] Field of Search ........................... 546/14; 424/258

[56] References Cited

FOREIGN PATENT DOCUMENTS

| 1432378 | 9/1973 | United Kingdom | 546/170 |
| 1463666 | 12/1974 | United Kingdom | 546/14 |
| 1463668 | 3/1975 | United Kingdom | 546/93 |
| 1465651 | 4/1975 | United Kingdom | 546/170 |
| 1495993 | 1/1976 | United Kingdom | 546/108 |

Primary Examiner—Robert T. Bond
Attorney, Agent, or Firm—Richard K. Jackson

[57] ABSTRACT

The invention provides new silyl derivatives of 5,6,7,8-tetrahydroquinolines and related compounds. The tetrahydroquinolines are substiuted at the 8-position by the group $SiR_3$ where R may be one of various hydrocarbon groups or an electron donating substituent. The 8-position may also carry a lithium, sodium or potassium atom. The new silyl derivatives may be prepared by treating a corresponding 8-lithio, sodio or potassio tetrahydroquinoline with a silyl halide $R_3SiHal$ followed by a metal compound R*M where M is sodium, potassium or lithium and R* is alkyl, cycloalkyl, aralkyl or aryl or an amine residue. The new silyl derivatives are useful intermediates for the preparation of known 5,6,7,8-tetrahydroquinline-8-nitriles, amides and thioamides employing an alkyl silyl isothiocyanate or cyanate. The nitriles and thioamides are anti-ulcer agents. The related compounds may be made by analogous methods.

19 Claims, No Drawings

SILYL COMPOUNDS

The invention relates to novel silyl derivatives of fused carbocyclic ring derivatives of pyridine processes using the novel derivatives.

In our United Kingdom Patent Specification No. 1463666 we described a process for preparing tetrahydroquinoline-8-thiocarboxamides, nitriles and carboxamides and related compounds by treating a corresponding sodio, lithio, potassio or magnesium halide derivative with a silyl compound of formula $R_xSi(N-CY)_{4-x}$ wherein R is alkyl, aryl or aralkyl, Y is oxygen or sulphur and x has a value from 0 to 3 and subjecting the product to hydrolysis or alcoholysis. The reaction is conducted under anhydrous conditions preferably in an inert solvent, for example, a hydrocarbon solvent such as benzene, toluene or n-hexane. This is a very short route for preparing tetrahydroquinoline-8-thiocarboxamides directly from the above mentioned metal derivatives of the corresponding tetrahydroquinolines. However we have found that the overall yields are usually lower than 50%. After extensive research and investigation of this reaction we have discovered that better yields can usually be obtained by using a novel silyl derivative of the tetrahydroquinoline or related compound and novel metallated derivatives thereof.

Accordingly, this invention provides in one aspect, new silyl compounds of formula I.

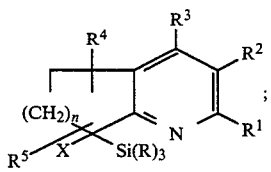

wherein $R^1$, $R^2$, $R^3$, $R^4$ and $R^5$ are the same or different and represent hydrogen or alkyl, cycloalkyl, aralkyl, or aryl radicals, any of which radicals may be substituted, or $R^1$ and $R^2$ taken together, or $R^2$ and $R^3$ taken together, form a 5, 6, or 7 membered ring which may be saturated or unsaturated and substituted or unsubstituted, and when $R^1$ and $R^2$ form a ring, the ring has the same number of carbon atoms as the ring carrying $R^4$, $R^4$ and $R^5$ may also represent alkoxy, n is 1, 2 or 3 and X is hydrogen or lithium, sodium or potassium and R is alkyl, cycloalkyl, aralkyl or aryl or R is selected from electron donating substituents including alkoxy, cycloalkoxy, aralkoxy, aryloxy, alkylthio, cycloalkylthio, aralkylthio, or arylthio or the group $R^bR^cN-$ wherein $R^b$ and $R^c$ are selected from alkyl, cycloalkyl, aryl and aralkyl or $R^b$ and $R^c$ may be joined to form a heterocyclic ring with the nitrogen atom (e.g., a piperidinyl Kor pyrrolidinyl ring, which may be substituted e.g., by alkyl).

The groups R are not necessarily all the same but it is preferred that $Si(R)_3$ is tri-loweralkyl silyl or more preferably trimethyl silyl.

When any of $R^1$, $R^2$, $R^3$, $R^4$, $R^5$ or R is an alkyl radical it is preferred that this is a lower alkyl radical of 1 to 6 carbon atoms which may have a straight or branched chain e.g., methyl, ethyl, n- and iso-propyl and n-, s- and t- butyl. When R, $R^4$ or $R^5$ is an alkoxy radical it is preferred that the radical is lower alkoxy in which the alkyl portion has 1 to 6 carbon atoms and is as defined above, for an alkyl radical.

When any of $R^1$, $R^2$, $R^3$, $R^4$, $R^5$ or R is a cycloalkyl radical such radicals having from 4 to 6 carbon atoms are preferred i.e. cyclobutyl, cyclopentyl or cyclohexyl.

An aralkyl group may be an arylalkyl group in which the alkyl portion is as described herein for an alkyl group. Preferred aralkyl groups are those having from 7-12 carbon atoms.

When any of $R^1$, $R^2$, $R^3$, $R^4$, $R^5$ or R is an aryl group it is preferably phenyl or substituted phenyl (substituted by e.g., alkyl, alkoxy, or trifluoromethyl.

Preferably the compound of formula I is a tetrahydroquinoline derivative i.e. n is 2.

The compounds of formula I may be prepared by treating a compound of formula II

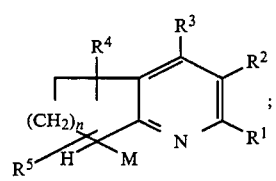

wherein M is sodium, potassium or lithium, and $R^1$, $R^2$, $R^3$, $R^4$, $R^5$ and n are as defined in connection with formula I with a silylating agent of formula $(R)_3SiHal$ where R is as defined previously and Hal is chlorine, bromine or iodine to obtain a compound I, wherein X is hydrogen, and if desired treating this with a metal compound R*M where M is sodium, potassium or lithium and R* is alkyl, cycloalkyl, aralkyl or aryl or an amine residue, to obtain a compound of formula I wherein X is sodium potassium or lithium.

The above reactions may be carried out in any suitable reaction medium solvent. Thus the first stage is conveniently carried out in a reaction medium comprising an ether solvent, preferably tetrahydrofuran but other cyclic ethers e.g., dioxan, may be used or dialkyl ethers, wherein the alkyl group has from 1 to 6 carbon atoms e.g., diethyl ether. Other reaction media which may be used are hydrocarbon solvents such as benzene, toluene or n-hexane. The reaction medium may comprise two or more of the above solvents.

Conveniently the starting material of formula II may be prepared in situ by reaction of a compound of formula II, wherein M is hydrogen with a suitable organometallic compound such as an alkyl, aryl or aralkyl lithium, sodium or potassium compound as described in UK Patent Specification No. 1432378 or using the modification described in UK Patent Specification No. 1463666, wherein a metal amide is reacted with a compound of formula II wherein M is hydrogen. The metal amide may be formed in situ and may be any of those described in UK Patent Specification No. 1463666 viz. an amide derived from a secondary amine such as a dialkylamine e.g. diethylamine, di-isopropylamine, ditertiary butylamine, di-n-decylamine, dicyclohexylamine, N-t-amyl-N-t-butyl-amine, N-isopropyl-N-cyclohexylamine, or N-(1-ethylcyclohexyl)-1,1,3,3-tetramethylbutylamine or a cyclic compound e.g. piperidine, or 2,2,6,6-tetramethylpiperidine. Alternatively any of the metal amides described in co-pending U.S. Ser. No. 472787 filed Mar. 7, 1983 may be used. These metal amides have the formula III

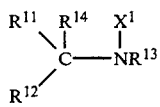

wherein $R^{14}$ is a straight or branched chain alkyl group of 1 to 6 carbon atoms or an aryl group, $R^{11}$ is hydrogen, aryl or a tertiary alkyl group of 4–6 carbon atoms, $R^{12}$ is aryl or a tertiary alkyl group of 4–6 carbon atoms, $R^{13}$ is a branched chain alkyl of 3 to 6 carbon atoms; $X^1$ is lithium, sodium or potassium. These metal amides are conveniently prepared by a novel process described in U.S. Ser. No. 472787, namely reacting a compound of formula IV.

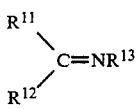

wherein $R^{11}$, $R^{12}$ and $R^{13}$ are as defined above with a metal alkyl $MR^{14}$ where $R^{14}$ is as defined above and M is lithium, sodium or potassium, in an inert non-polar solvent to obtain a compound of formula III.

Since the starting compound of formula II is conveniently prepared in situ using the metal alkyl in a hydrocarbon solvent and the silylation reaction is conveniently carried out in an ether, the reaction medium will often comprise a hydrocarbon/ether solvent. Furthermore when a compound of formula I wherein X is sodium, potassium or lithium is desired the reaction with the metal compound R*M may be carried out by adding the metal compound in a hydrocarbon solvent, e.g., n-hexane, to a solution of compound I where X is hydrogen, prepared in situ. As will be apparent a metal amide, such as one discussed above, may be used as the compound R*M in the preparation of a compound of formula I where X is sodium, potassium or lithium. However, there will not normally be any advantage in using a metal amide and it is preferable to use a metal alkyl, aryl or aralkyl in both the preparation of the starting compound of formula II and the end product of formula I where X is sodium, potassium or lithium.

The new chemical intermediates of formula I may be used in various chemical processes which are all included in the invention.

Accordingly this invention provides in one aspect, a process for preparing compounds of formula V

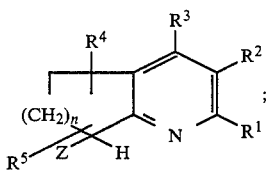

or acid addition salts thereof, wherein $R^1$, $R^2$, $R^3$, $R^4$, $R^5$ and n are as defined in connection with formula I and Z is CN, $CONH_2$ or $CSNH_2$ which process comprises treating a compound of formula I as defined above, wherein X is sodium, potassium or lithium with a silyl compound of formula VI $R_x{}^aSi(NCY)_{4-x}$ wherein $R^a$ is selected from electron donating substituents, [including alkoxy, cycloalkoxy, aralkoxy, aryloxy, alkylthio, cycloalkylthio, aralkylthio, arylthio] or the group $R^bR^cN-$ wherein $R^b$ and $R^c$ are selected from alkyl, cycloalkyl, aryl and aralkyl or $R^b$ and $R^c$ may be joined to form a heterocyclic ring with the nitrogen atom (e.g., a piperidinyl or pyrrolidinyl ring, which may be substituted e.g., by alkyl), and hydrocarbon substituents selected from alkyl, cycloalkyl, aralkyl or aryl, Y is oxygen or sulphur, x has a value from 0–3, then subjecting the product to hydrolysis or alcoholysis with the proviso that when a compound of formula V in which Z is CN is desired the molar ratio of compound $R_x{}^aSi(NCY)_{4-x}$ to compound I is at least 2:1 and x is 3 and Y is S and if desired isolating the product as an acid addition salt.

The compounds of formula V are known compounds which are described in UK Patent Specification Nos. 1463666, 1432378, 1463668, 1465651 and 1495993. The compounds of formula V in which Z is $CSNH_2$ are anti-ulcer agents which display anti-ulcer and/or anti-secretory activity in standard test procedures. The nitriles of formula V where Z is CN are intermediates for the corresponding thioamides and usually also display anti-ulcer and/or anti-secretory activity. The amides of formula V in which Z is $CONH_2$ are intermediates for the corresponding nitriles and thioamides.

The preferred reaction medium for the above process is an ether solvent e.g., a dialkyl ether, wherein the alkyl group has from 1 to 6 carbon atoms, e.g., diethyl ether, or a cyclic ether such as tetrahydrofuran or dioxan. Other reaction media which may be used are hydrocarbon solvents such as benzene, toluene or n-hexane. Mixtures of two or more of the above mentioned solvents may be used.

In a preferred aspect of this process a compound $R_3{}^aSiNCY$ is used in which one group $R^a$ is an electron donating substituent or a branched chain alkyl (e.g. $C_3$–$C_{10}$), branched aralkyl, cycloalkyl (e.g. $C_4$–$C_8$), or aryl and the other two groups $R^a$ are alkyl, e.g., t-butyldimethylsilyl isothiocyanate.

When $R^a$, $R^b$ or $R^c$ is an alkyl radical, an aryl radical, an aralkyl radical or a cycloalkyl radical the radical may be as defined for $R^1$, $R^2$, $R^3$, $R^4$ and $R^5$. When $R^a$ is an alkoxy radical, the radical may be $C_1$–$C_{10}$ but is preferably as defined for $R^4$ and $R^5$. When R or $R^a$ is an alkylthio group the alkyl portion is as defined for an alkyl group and $R^a$ may be $C_1$–$C_{10}$. If R or $R^a$ is cycloalkoxy or cycloalkylthio the cycloalkyl portion of this group may be as described for a cycloalkyl group and $R^a$ may be $C_4$ to $C_8$.

An aralkyloxy or aralkylthio group may be such a group in which the aralkyl portion is as described for an aralkyl group. The aryl portion is preferably phenyl. An aryloxy or arylthio group may be such a group in which the aryl portion is as defined for an aryl group, 2,6-disubstituted phenyl being a preferred aryl portion.

When it is desired to prepare nitriles of formula V by the above reaction instead of using 2 or more moles of compound $R_x{}^aSi(NCY)_{4-x}$ to complete I the reaction may be carried out by reacting 1 mol of compound $R_x{}^aSi(NCY)_{4-x}$ with compound I wherein X is Na, K or Li followed by addition of 1 or more mols of $R_x{}^aSiHal_{4-x}$ wherein $R^a$ and x are as defined previously and Hal is chlorine or bromine, $R^a$ and x in this compound need not be the same as in the reagent $R_x{}^aSi(NCY)_{4-x}$. This process for preparing nitriles is also included in the invention.

The new chemical intermediates of formula I may also be used in a variety of reactions in addition to those already discussed. Examples of reactions are given below:

(1) To prepare substituted thioamides corresponding to those of formula V where Z is $CSNHR^d$ and $R^d$ is alkyl instead of Z is $CSNH_2$. These substituted thioamides may be obtained by treating a compound of formula I, wherein X is Na, K or Li with a compound of formula $R^dNCS$ followed by treating the product with hydrogen ions. The source of hydrogen ions may be water, an alcohol e.g., a lower alkanol of 1–6 carbon atoms or an aqueous mineral acid e.g., a hydrohalic acid, preferably hydrochloric acid, or an organic acid such as acetic acid.

(2) To prepare substituted amides corresponding to those of formula V where Z is $CONHR^d$ and $R^d$ is alkyl, instead of X is $CONH_2$. These substituted amides may be obtained by treating a compound of formula I wherein X is Na, K or Li with a compound of formula $R^dNCO$, e.g. methyl isocyanate followed by treating the product with hydrogen ions as discussed in paragraph (1) above.

(3) To prepare carboxylic acids, their salts and esters of formula V wherein Z is $CO_2H, CO_2M$ where M is sodium potassium or lithium or $CO_2R^e$ and $R^e$ is alkyl, aralkyl or aryl. The esters may be prepared by treating a compound of formula I wherein X is Na, K or Li with a haloformate $HalCO_2R^e$ where Hal is chlorine, bromine or iodine and $R^e$ is as defined previously followed by treating the product with hydrogen ions e.g. as discussed in paragraph (1) above. The carboxylic acid salts may be obtained by treating a compound of formula I wherein X is Na, K or Li with carbon dioxide. These salts may be converted to the free acid by treatment with acid e.g., mineral acids, e.g., of the type discussed in (1) above.

The three processes described above are all included in the invention.

One advantage of the new silyl compounds of formula I when used to prepare compounds of formula V is that there is a reduction in the tendency for side reactions to occur. For example, in the process of UK Patent Specification No. 1463666 it has been found that with certain alkyl substituted tetrahydroquinolines (e.g., 4-methyl compounds) the yields of final product are less than expected. This is due, at least in part, to the tetrahydro-8-lithio-4-methylquinoline being converted to a 4-lithiomethyl-tetrahydroquinoline. It has been found that the novel tetrahydro-8-lithio-4-methyl-8-silyl-quinoline does not undergo a similar reaction so that the 4-methyl group is not lithiated.

THE FOLLOWING EXAMPLES ILLUSTRATE THE INVENTION

Example 1

5,6,7,8-Tetrahydro-8-trimethylsilyl-3-methylquinoline

A mixture of 5,6,7,8-tetrahydro-3-methylquinoline (29.4 g, 0.2 M) and tetrahydrofuran (THF) (50 ml) was added to a mixture of a 1.55 molar solution of butyl lithium in hexane (129 ml, 0.2 M) and THF (50 ml), maintained below 10°. After 0.5 hour the mixture was blown over by inert gas onto a mixture of trimethylsilyl chloride (50 ml, 0.4 M) in the THF (100 ml), maintained below 10°. After 0.5 hour, the mixture was evaporated and the residue extracted with hexane. The hexane extracts were evaporated with the residue distilled to give the title compound (40 g, 91%) b.p. 118°–124°/5 mbar. (Found: C70.9; H,9.65; N,6.4% $C_{13}H_{21}$ NSi requires: C,71.2; H,9.6; N6.4%).

Example 2

5,6,7,8-Tetrahydro-8-trimethylsilyl-4-methylquinoline

The title compound was prepared in a similar manner to that described in Example 1 using 5,6,7,8-tetrahydro-4-methylquinoline (0.1 M), butyl lithium (0.11 M) and trimethylsilyl chloride (0.2 M) in 95% yield b.p. 80°/0.1 mm (Found: C71.1; H,9.3; N,6.0 $C_{13}N_{21}$ NSi requires: C71.2; H,9.6; N,6.4%).

Example 3

5,6,7,8-Tetrahydro-3-methylquinoline-8-thiocarboxamide

A mixture of a 1.55 molar solution of butyl lithium in hexane (6.45 ml, 10 mM) and THF (10 ml) maintained below 10° was treated with a solution of 5,6,7,8-tetrahydro-8-trimethylsilyl-3-methylquinoline (2.2 g, 10 mM) in THF (10 ml) to obtain 5,6,7,8-tetrahydro- -8-lithio-8-trimethylsilyl-3-methylquinoline. After 0.5 hour a 22% solution of t-butyldimethylsilyl isothiocyanate in benzene (6.9 g, 10 mM) was added dropwise. After 0.5 hour the reaction mixture was quenched with 2N hydrochloric acid (25 ml) and after 1 hour the aqueous layer was separated, basified (to pH9) and extracted with dichloromethane (2×50 ml). The organic extracts were dried and evaporated to give the title thioamide (2.1 g, c 100%). Recrystallisation from benzene gave analytically pure material (1.9 g, 88%) m.p. 153°, identical to authentic material (Found: C63.7; H,6.9; N,13.4% $C_{11}H_{14}N_2S$ requires: C64.0; H,6.8; N,13.6%).

Example 4

5,6,7,8-Tetrahydro-4-methylquinoline-8-thiocarboxamide

A mixture of a 1.55 molar solution of n-butyl lithium in hexane (14.2 ml, 22mM) and THF (25 ml), maintained below 5° was treated with a solution of 5,6,7,8-tetrahydro-8-trimethylsilyl- 4-methylquinoline (4.4 g, 20 mM) in THF (10 ml) to give 5,6,7,8-tetrahydro-8-lithio-8-trimethylsilyl -4-methylquinoline. After 0.5 hour a solution of t-butyldimethylsilyl isothiocyanate (22 mM) in benzene (15 ml) was added; after a further 0.5 hour the mixture was quenched with 0.5 N hydrochloric acid (60 ml). After 1 hour toluene (50 ml) was added, the aqueous layer was separated, adjusted to pH10 and extracted with dichloromethane. The organic extract was evaporated and chromatographed on silica using ether as eluant. The title thioamide was obtained in 60% yield (identical to authentic material) together with the corresponding nitrile (20%) and 5,6,7,8-tetrahydro-4-methylquinoline (20%).

Example 5

5,6,7,8-Tetrahydro-4-methylquinoline-8-(N-methylthiocarboxamide

A mixture of a 1.55 molar solution of n-butyl lithium in hexane (12.9 ml, 20 mM) and THF (10 ml), maintained at 5° was treated with a solution of 5,6,7,8-tetrahydro-8-trimethylsilyl-4-methylquinoline (4.34 g, 20 mM) to obtain 5,6,7,8-tetrahydro-8-lithio-8-trimethylsilyl-4-methyl-quinoline. After 0.5 hour a solution of methyl isothiocyanate (1.46 g, 20 mM) in THF (10 ml) was added and after a further 0.5 hour the mixture was quenched with N hydrochloric acid (50 ml). Ether was added and the aqueous layer was separated, adjusted to pH10 and extracted with dichloromethane(2×50 ml). The organic extract was dried, evaporated, dissolved in ethyl acetate and passed through a short pad of silica. Evaporation of the eluate followed by recrystallisation from ethyl acetate gate the title compound (2.4 g) m.p. 151°–3°. The hydrochloride (from propan-2-ol) had m.p. 240°–5°(d) (Found: C,56.5; H,6.6; N,10.6% $C_{12}H_{16}N_2SHCl$ requires C,56.1; H,6.7; N,10.9%).

Example 6
8-Cyano-5,6,7,8-tetrahydro-3-methylquinoline

A mixture of a solution of 1.5 molar n-butyl lithium in hexane (12.9 ml, 20 mM) and THF (10 ml), maintained at 5° was treated with a solution of 5,6,7,8-tetrahydro-8-trimethylsilyl-3-methylquinoline (4.34 g 20 mM) to obtain 5,6,7,8-tetrahydro-8-lithio-8-trimethylsilyl-3-methylquinoline. After 0.5 hour a solution of t-butyl-dimethylsilyl isothiocyanate (7.0 g 40 mM) was added and the mixture allowed to warm to 20° over 12 hours. The reaction was quenched with 2N hydrochloric acid and stirred 1 hour. The mixture was extracted with ether, the aqueous phase adjusted to pH10 and extracted with ether. The organic extracts were dried and evaporated to give the title compound (3 g, 85%) identical with authentic material.

Example 7
5,6,7,8-Tetrahydro-8-dimethoxymethylsilyl-3-methylquinoline

The title compound was prepared in a similar manner to that described in Example 1 using 5,6,7,8-tetrahydro-3-methylquinoline (0.01 M), butyl lithium (0.01 M) and dimethoxymethylsilyl chloride (0.015 M). The sample was distilled twice using a kugelrohr apparatus to give the title compound (0.25 g) bp 110°–120° C./0.5 mm.

Example 8
5,6,7,8-Tetrahydro-3-methylquinoline-8-(N-methyl)carboxamide

8-Lithio-5,6,7,8-tetrahydro-3-methyl-8-trimethylsilylquinoline, prepared as in Example 3, is treated at −20° C. under nitrogen with a solution of 1 equivalent of methyl isocyanate in tetrahydrofuran. After this addition the mixture is allowed to warm to ambient temperature and the solvent removed by evaporation. The residue is dissolved in 2NHCl and washed with ether, basified with $Na_2CO_3$ and extracted with chloroform. The extracts are dried and evaporated and the residue purified by chromatography to give the title compound.

Example 9
Methyl-5,6,7,8-tetrahydro-3-methylquinoline-8-carboxylate

8-Lithio-5,6,7,8-tetrahydro-3-methyl-8-trimethylsilylquinoline, prepared as in Example 3, is treated with 1 equivalent of methyl chloroformate in THF at −20° C. under nitrogen. After the addition the mixture is allowed to warm to ambient temperature and the solvent removed by evaporation. The residue is dissolved in 2NHCl and washed with ether basified with $Na_2CO_3$ and extracted with chloroform. The extracts are dried and evaporated. Distillation of the residue gives the title compound as a pale yellow oil bp 120°/0.25 mm.

Example 10
Methyl-5,6,7,8-tetrahydro-3-methylquinoline-8-carboxylate

8-Lithio-5,6,7,8-tetrahydro-3-methyl-8-trimethylsilylquinoline, prepared as in Example 3, is blown over onto ether at 0° C. through which a vigorous stream of $CO_2$ gas is being passed. After the addition the resulting solid, lithium 5,6,7,8-tetrahydro-3-methyl-8-trimethylsilylquinoline-8-carboxylate, is removed by filtration. This is then dissolved in methanol (200 ml) and the solution treated with HCl gas to excess and heated at reflux for 4 hours. The solvent is removed in vacuo and the residue dissolved in water (50 ml), made alkaline with 2N NaOH and extracted with chloroform. The extracts are dried, evaporated and the residue distilled to give the title compound as a pale yellow oil bp 120°/0.25 mm.

We claim:

1. A silyl compound of formula I

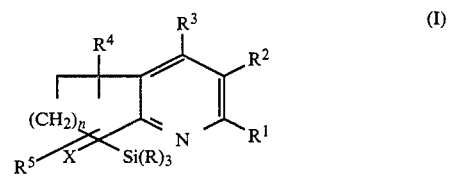

cycloalkyl, $C_7$–$C_{12}$ aralkyl or phenyl radicals, any of which cyclic radicals may be substituted by $C_1$–$C_6$ alkyl, $C_1$–$C_6$ alkoxy or trifluoromethyl; or $R^1$ and $R^2$ taken together or $R^2$ and $R^3$ taken together, with the carbon atoms to which they are attached, form a 5-, 6-, or 7-membered carbocyclic ring, and when $R^1$ and $R^2$ form a ring, the ring has the same number of carbon atoms as the ring carrying $R^4$; or $R^4$ and $R^5$ may also represent $C_1$–$C_6$ alkoxy;

n is one of the integers 1, 2 or 3;

X is hydrogen or lithium, sodium or potassium; and

R is $C_1$–$C_6$ alkyl, $C_4$–$C_6$ cycloalkyl, $C_7$–$C_{12}$ aralkyl or phenyl which may be substituted by $C_1$–$C_6$ alkyl, $C_1$–$C_6$ alkoxy or trifluoromethyl; or R is an electron dontating group selected from $C_1$–$C_6$ alkoxy, $C_4$–$C_6$ cycloalkoxy, $C_7$–$C_{12}$ aralkoxy, phenoxy which may be substituted by $C_1$–$C_6$ alkyl, $C_1$–$C_6$ alkoxy or trifluoromethyl, $C_1$–$C_6$ alkylthio, $C_4$–$C_6$ cycloalkythio, $C_7$–$C_{12}$ aralkythio, the group $R^bR^cN$- wherein $R^b$ and $R^c$ are selected from $C_1$–$C_6$ alkyl, $C_4$–$C_6$ cycloalkyl, phenyl and $C_7$–$C_{12}$ aralkyl or $R^b$ and $R^c$ may be joined to form a pyrrolidine or piperidine with the nitrogen atom ring, which pyrrolidine or piperidine ring may be substituted by $C_1$–$C_6$ alkyl or $C_4$–$C_6$ cycloalkyl.

2. A compound as claimed in claim 1, wherein $Si(R)_3$ is triloweralkylsilyl, in which each said lowerakly group is of from 1 to 6 carbon atoms.

3. A compound as claimed in claim 2, wherein $Si(R)_3$ is trimethysilyl.

4. A compound as claimed in claim 1 wherein the compound is a 5,6,7,8-tetrahydroquinoline derivative.

5. 5,6,7,8-Tetrahydro-8-trimethylsilyl-3-methyl quinoline.

6. 5,6,7,8-Tetrahydro-8-dimethoxymethysilyl-4-methyl quinoline.

7. 5,6,7,8-Tetrahydro-8-dimethoxymethylsilyl-3-methyl quinoline.

8. A process for preparing a compound as claimed in claim 1, which process comprises treating a compound of formula II

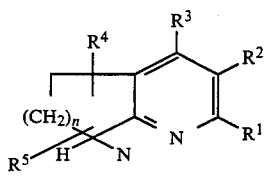

wherein M is sodium, potassium or lithium; $R^1$, $R^2$, $R^3$, $R^4$, $R^5$ and n are as defined in claim 1 in connection with formula I with a silylating agent of formula $(R)_3SiHal$ where R is as defined in claim 1 and Hal is chlorine, bromine or iodine to obtain a compound I, as defined in claim 1 wherein X is hydrogen, and if desired treating this with a metal compound R*M where M is sodium, potassium or lithium and R* is $C_1$-$C_6$ alkyl, $C_4$-$C_6$ cycloalkyl, $C_7$-$C_{12}$ aralkyl, or phenyl, which may be substituted by $C_1$-$C_6$ alkyl, $C_1$-$C_6$ alkoxy or trifluoromethyl, or a secondary amine, to obtain a compound of formula I as defined in claim 1 wherein X is sodium, potassium or lithium.

9. A process as claimed in claim 8, when carried out in a reaction medium comprising an ether solvent.

10. A process as claimed in claim 9, wherein the reaction medium comprises an ether and a hydrocarbon solvent.

11. A process for preparing compounds of formula V

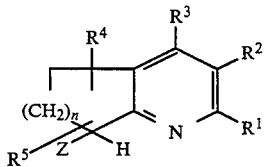

or acid addition salts thereof, wherein $R^1$, $R^2$, $R^3$, $R^4$, $R^5$ and n are as defined in claim 1 and Z is CN, $CONH_2$ or $CSNH_2$, which process comprises treating a compound of formula I as defined in claim 1, wherein X is sodium, potassium or lithium with a silyl compound of formula VI $(R^a)_xSi(NCY)_{4-x}$ wherein $R^a$ is an electron donating group, independently selected from $C_1$-$C_{10}$ alkoxy, $C_4$-$C_8$ cycloalkoxy, $C_7$-$C_{12}$ aralkoxy, aryloxy, the group $R^bR^cN$ wherein $R^b$ and $R^c$ are selected from $C_1$-$C_6$ alkyl, $C_4$-$C_6$ cycloalkyl, phenyl, which may be substituted by $C_1$-$C_6$ alkyl, $C_1$-$C_6$ alkoxy or trifluoromethyl, and $C_7$-$C_{12}$ aralkyl or $R^b$ and $R^c$ may be joined to form a 5- or 6-membered ring with the nitrogen atom, $C_1$-$C_{10}$ alkylthio, $C_4$-$C_8$ cycloalkylthio, $C_7$-$C_{12}$ aralkylthio, phenylthio which may be substituted by $C_1$-$C_6$ alkyl, $C_1$-$C_6$ alkoxy or thifluoroemthyl, or hydrocarbon substituents selected from $C_1$-$C_{10}$ alkyl, $C_4$-$C_8$ cycloalkyl, $C_7$-$C_{12}$ aralkyl or phenyl which may be substituted by $C_1$-$C_6$ alkyl, $C_1$-$C_6$ alkoxy or trifluoromethyl, Y is oxygen or sulphur, x has a value from 0-3, then subjecting the product to hydrolysis or alcoholysis with the proviso that when a compound of formula V in which Z is CN is desired the molar ratio of compound $(R^a)_x$-$Si(NCY)_{4-x}$ to compound I is at least 2:1 and x is 3 Y is S and if desired isolating the product as an acid addition salt.

12. A process as claimed in claim 11, when carried out in a reaction medium comprising an ether solvent.

13. A process as claimed in claim 12, when carried out in a reaction medium comprising an ether and a hydrocarbon solvent.

14. A process as claimed in claim 11 wherein the compound of formula VI is $(R^a)_3SiNCY$, wherein one group $R^a$ is an electron donating group as defined in claim 11 or a branched chain $C_3$-$C_{10}$ alkyl, branched $C_8$-$C_{12}$ aralkyl, $C_4$-$C_8$ cycloalkyl, or phenyl which may be substituted by $C_1$-$C_6$ alkyl, $C_1$-$C_6$ alkoxy or trifluoromethyl, and the other two groups $R^a$ are $C_1$-$C_6$ alkyl.

15. A process as claimed in claim 14, wherein the compound of formula VI is t-butyldimethylsilylisothiocyanate.

16. A processing for preparing a compound of the formula

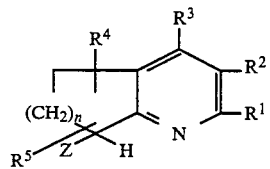

wherein Z is $CSNHR^d$ where $R^d$ is $C_1$-$C_6$ alkyl, $R^1$, $R^2$, $R^3$, $R^4$ and $R^5$ are, independently, hydrogen or $C_1$-$C_6$ alkyl, $C_4$-$C_6$ cycloalkyl, $C_7$-$C_{12}$ aralkyl or phenyl radicals, any of which cyclic radicals may be substituted by $C_1$-$C_6$ alkyl, $C_1$-$C_6$ alkoxy or trifluoromethyl; or $R^1$ or $R^2$ taken together or $R^2$ and $R^3$ taken together, with the carbon atoms to which they are attached, form a 5-, 6- or 7-membered carbocyclic ring and when $R^1$ and $R^2$ form a ring, the ring has the same number of carbon atoms as the ring carrying $R^4$; or $R^4$ and $R^5$ may also represent $C_1$-$C_6$ alkoxy and n is one of the integers 1, 2 or 3, which process comprises treating a compound of formula I as defined in claim 1 and wherein X is sodium, lithium or potassium with a compound of formula $R^dNCS$ followed by treating the product with hydrogen ions.

17. A process as claimed in claim 16, wherein the compound $R^dNCS$ is methylisothiocyanate.

18. A process for preparing a compound of the formula

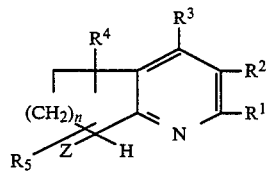

wherein Z is $CONHR^d$ where $R^d$ is $C_1$-$C_6$ alkyl, $R^1$, $R^2$, $R^3$, $R^4$ and $R^5$ are, independently, hydrogen or $C_1$-$C_6$ alkyl, $C_4$-$C_6$ cycloalkyl, $C_7$-$C_{12}$ aralkyl or phenyl radicals, any of which cyclic radicals may be substituted by $C_1$-$C_6$ alkyl, $C_1$-$C_6$ alkoxy or trifluoromethyl; or $R^1$ and $R^2$ taken together or $R^2$ and $R^3$ taken together, with the carbon atoms to which they are attached, form a 5-, 6- or 7-membered carbocyclic ring and when $R^1$ and $R^2$ form a ring, the ring has the same number of carbon atoms as the ring carrying $R^4$; or $R^4$ and $R^5$ may also represent $C_1$-$C_6$ alkoxy and n is one of the integers 1, 2 or 3, which process comprises treating a compound of formula I as defined in claim 1 and wherein X is sodium, lithium or potassium, with a compound of formula $R^dNCO$, where $R^d$ is $C_1$-$C_6$ alkyl, followed by treating the product with hydrogen ions.

19. A process as claimed in claim 18, wherein the compound $R^dNCO$ is methyl isocyanate.

* * * * *

UNITED STATES PATENT AND TRADEMARK OFFICE
CERTIFICATE OF CORRECTION

PATENT NO. : 4,577,022
DATED : March 18, 1986
INVENTOR(S) : Roger Crossley and Robin G. Shepherd It is certified that error appears in the above-identified patent and that said Letters Patent are hereby corrected as shown below:

Column 1, line 55, delete "K".

Column 8, Claim 1, after the structural formula, insert -- wherein $R^1$, $R^2$, $R^3$, $R^4$ and $R^5$ are independently hydrogen or $C_1$-$C_6$ alkyl, $C_4$-$C_6$ -- ; line 52, after "joined", insert -- with the nitrogen atom -- ; line 53, after "piperidine", delete "with the nitrogen atom".

Column 8, Claim 6, line 65, delete "dimethoxymethylsilyl" and insert -- trimethylsilyl -- .

Column 9, Claim 8, in the structural formula, the left-hand ring should have a substituent "M", thusly --

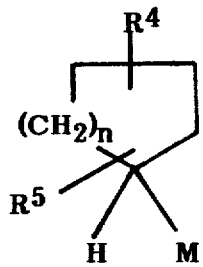

Column 9, Claim 11, line 56, delete "thifluoroemthyl" and insert -- trifluoromethyl -- .
Column 10, Claim 16, line 1, delete "processing" and insert -- process -- .

Signed and Sealed this

Twelfth Day of August 1986

[SEAL]

Attest:

DONALD J. QUIGG

Attesting Officer   Commissioner of Patents and Trademarks